United States Patent [19]

Bidell et al.

[11] Patent Number: 5,366,621
[45] Date of Patent: Nov. 22, 1994

[54] CHROMATOGRAPHY COLUMN

[75] Inventors: Christopher R. Bidell, Kings Stanley; Colin K. Lanyl, Stroud; Anthony F. Mann, Malmesbury; Phillip Stafford, Stroud, all of England

[73] Assignee: Amicon Limited, Stonehouse, England

[21] Appl. No.: 144,456

[22] Filed: Oct. 28, 1993

Related U.S. Application Data

[63] Continuation of Ser. No. 8,279, Jan. 25, 1993, abandoned, which is a continuation of Ser. No. 757,871, Sep. 11, 1991, abandoned.

[30] Foreign Application Priority Data

Sep. 9, 1990 [GB] United Kingdom ............... 9020451.2

[51] Int. Cl.$^5$ ............................................. B01D 15/08
[52] U.S. Cl. ................................. 210/198.2; 210/656
[58] Field of Search ..................... 210/656, 189, 198.2, 210/232, 238, 450; 96/101; 422/76

[56] References Cited

U.S. PATENT DOCUMENTS

| | | | |
|---|---|---|---|
| 3,487,938 | 1/1970 | Patterson | 210/198.2 |
| 4,026,803 | 5/1977 | Abrahams | 210/198.2 |
| 4,070,285 | 1/1978 | Abrahams | 210/198.2 |
| 4,093,550 | 6/1978 | Stahl | 210/198.2 |
| 4,187,177 | 2/1980 | Stahl | 210/198.2 |
| 4,250,035 | 2/1981 | McDonald | 210/198.2 |
| 4,280,905 | 7/1981 | Gunkel | 210/198.2 |
| 4,283,280 | 8/1981 | Brownlee | 210/198.2 |
| 4,361,482 | 11/1982 | Teetz | 210/198.2 |
| 4,394,263 | 7/1983 | Dosch | 210/198.2 |
| 4,461,710 | 7/1984 | Erickson | 210/189 |
| 4,476,017 | 10/1984 | Scharff | 210/198.2 |
| 4,478,715 | 10/1984 | Goodnight | 210/198.2 |
| 4,597,866 | 7/1986 | Couillard | 210/198.2 |
| 4,769,141 | 9/1988 | Couillard | 210/198.2 |
| 4,846,970 | 7/1989 | Bertelsen | 210/232 |
| 4,861,473 | 8/1989 | Shackelford | 210/198.2 |
| 4,865,728 | 9/1989 | Larsson | 210/198.2 |
| 4,888,112 | 12/1989 | Krunwald | 210/450 |
| 4,891,133 | 1/1990 | Colvin | 210/198.2 |
| 4,922,977 | 5/1990 | Colton | 407/49 |
| 4,927,531 | 5/1990 | Sakamoto | 210/198.2 |

FOREIGN PATENT DOCUMENTS

| | | | |
|---|---|---|---|
| 0008921 | 8/1979 | European Pat. Off. | 210/198.2 |
| 0049850 | 10/1981 | European Pat. Off. | 210/198.2 |
| 0108242 | 9/1983 | European Pat. Off. | 210/198.2 |
| 61-61346 | 12/1986 | Japan | 210/198.2 |
| 62-3380 | 1/1987 | Japan | 210/198.2 |
| 62-42052 | 2/1987 | Japan | 210/198.2 |

OTHER PUBLICATIONS

Abstract of Swedish Patent No. 459396 published Jul. 3, 1989.

Snyder, Introduction to Modern Liquid Chromotography, John Wiley & Sons, Inc. New York, N.Y., 1979, pp. 203–204.

Primary Examiner—Ernest G. Therkorn
Attorney, Agent, or Firm—Nicholas P. Triano, III; William L. Baker

[57] ABSTRACT

A chromatography column piston 14 is adjustable in height within the column tube 4 by means of a friction clamp 22 which furthermore includes a threaded engagement with the associated end cap 8 of the column. As a result, with the friction clamp released the piston rod 16 can be rapidly traversed to or near a desired position, and the clamp then engaged following which cooperation of said threads allows fine tuning of the level of the piston 14 by fine adjustment of the position of the friction clamp relative to the end cap 8.

9 Claims, 3 Drawing Sheets

CHROMATOGRAPHY COLUMN

This is a continuation of application Ser. No. 08/008,279 filed on Jan. 25, 1993, which is a continuation of application Ser. No. 07/757,871 filed Sept. 11, 1991, now abandoned.

The present invention relates to a chromatography column which can more readily be packed and repacked than has hitherto been possible.

Chromatography columns of various sizes are known for use in, on the one hand, laboratories where the separation of a material into its constituents is carried out for analytical purposes and, on the other hand, in factory installations where the separating action is used for preparation of products such as the constituents of human blood.

The development of chromatography columns has aimed at providing ease of operation and various additional benefits which have particular commercial importance. These include: (a) the ability to be sterilized by autoclaving (b) improved sanitation by virtue of design features giving less carryover of product from one batch to the next, (c) the ability to resist solvents which may be used in the material to be separated, (d) conformity to food grade FDA regulations, (e) an improved pressure tolerance, and (f) lower cost.

It is an object of the present invention to provide a chromatography column in which the tedious operation of winding the piston along the column tube by a lead screw action during packing or unpacking can be avoided, while still giving the degree of fine adjustment of the piston position deriving from a screw thread traversing action.

Accordingly, the present invention provides a chromatography column including: a column tube; a movable piston within the column tube; an axially slidable piston rod carrying said piston; a releasable friction clamp for releasing said piston rod for rapid axial traversing of the piston and for clamping the piston rod at or near a desired final position; and means for fine adjustment of the position of the friction clamp axially relative to the column tube, for fine positioning of the piston relative to the column tube.

BRIEF DESCRIPTION OF THE DRAWINGS

In order that the present invention may more readily be understood the following description is given, merely by way of example, with reference to the accompanying drawings, in which.

DESCRIPTION OF THE PREFERRED EMBODIMENTS

Figure 1:
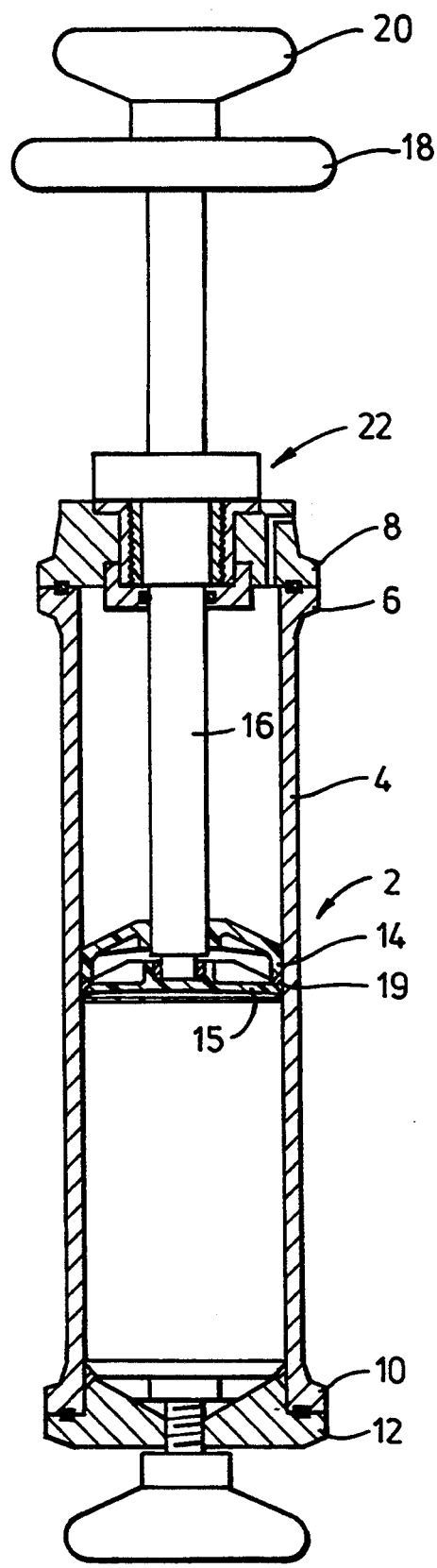
FIG. 1 is a longitudinal sectional view of a chromatography column embodying the present invention.

Referring now to the drawings, FIG. 1 shows the chromatography column 2 in accordance with the present invention as comprising a column tube 4 having at its upper end an end flange 6 for clamping to a corresponding flange of an end cap 8, and at its lower end an end flange 10 for clamping to the flange of a bottom end cap 12. Clamping at both ends is by means of a clamp (not shown) which may be a chain clamp or a C-clamp. Traversing along the column tube 4 is a piston 14 on an unthreaded piston rod 16, controlled by a wheel 18 which can be used both to press the piston rod axially up and down the column tube 4 and to rotate the piston rod 16, when appropriate.

The piston rod also has at its upper end a control wheel 20 for operating the seal on the piston, for example as is described and claimed in our co-pending application Ser. No. 9020450.4. This seal 19 is shown in FIG. 1 and is capable of being compressed axially to result in radial expansion to effect a seal against the inner face of the column tube 4. The sealing face (i.e. the substantially cylindrical radially outer face) of the seal 19 may be coated with polytetrafluoroethylene or may be formed by a sheet of polytetrafluoroethylene embedded in the body of the resilient seal material (which may be, for example, an ethylene propylene rubber silicone rubber or the thermoplastic rubber available from Monsanto Polymer Products Co., and known by the Trade Mark Santoprene). This preferred seal is self-compensating to the extent that an increase in pressure on the bed below the piston 14 can drive the lower part 15 of the piston upwardly against the upper part in order to increase the axial compression on the seal and hence to thrust the polytetrafluoroethylene-coated outer face more firmly against the radially inner face of the column tube 4 to ensure that the increased pressure cannot result in gas flow past the seal 19.

The upper end cap 8 of the column is associated with an adjuster mechanism 22 which can be clamped to provide for threaded fine adjustment of the position of the piston rod 16 or released in order to allow the piston rod to be rapidly traversed up and down the column tube 4, during the re-packing and unpacking operations.

Figure 2:
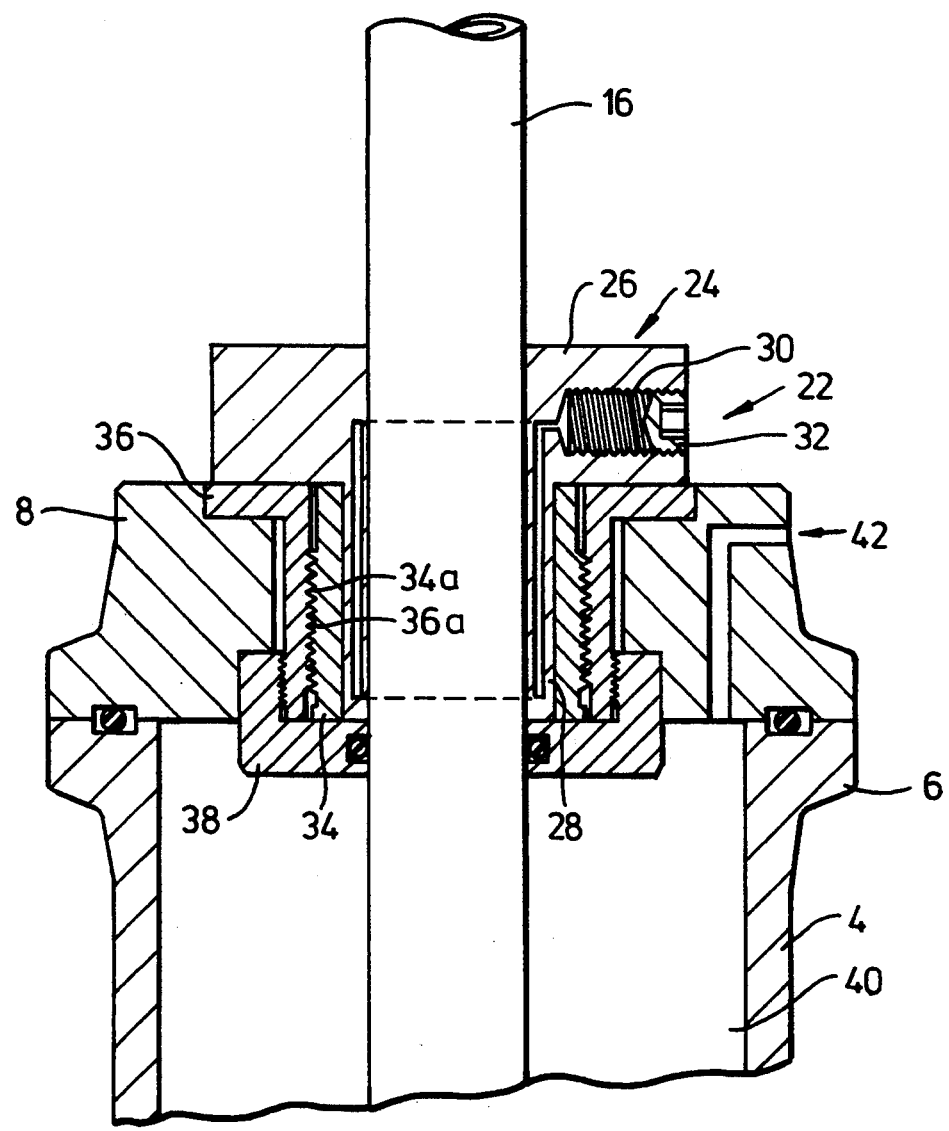
FIG. 2 is a detail of the top end cap of the column tube, shown in FIG. 1.

The clamping and adjustment mechanism 22 is better illustrated in FIG. 2 as comprising a clamp bush 24 having a collar section 26 and a skirt section 28, with an annular space within both the skirt section 28 and the radially inner part of the collar section 26, this internal space being in communication with a bore 30 in which a hexagon socket cap screw 32 is threadedly engageable. The clamp bush 24 is preferably made of stainless steel for best resistance to attack by corrosive fluids likely to be used in the chromatography separation operation.

Shrunk around the skirt section 28 of the clamp bush 24 is a sleeve 34 which is externally threaded to engage the internal threads of a jacking bush 36 clamped in the body of the end plug 8.

Such clamping of the jacking bush 36 in the end cap is achieved by virtue of a nut 38 having a threaded skirt portion which seats in an appropriate annular recess in the underside of the end cap 8 and has its internal threads able to engage limited external threading at the free end of the cylindrical projection of the jacking bush 36. When the nut 38 is screwed right home, the jacking bush 36 is held in situ in the end cap 8.

Because the sleeve 34 is shrunk on to the skirt portion 28 of the clamp bush 24, rotation of the clamp bush 24 causes "jacking" up or down (raising and lowering) of both the clamp bush and the shrunk-on sleeve 34 by engagement of the external threads of the sleeve 34 with the internal threading of the jacking bush 36. Thus, when the piston rod 16 is clamped to the clamp bush 24, rotation of the piston rod will result in fine vertical adjustment of its position, the fineness of this adjustment depending on the pitch of "jacking" of the external threads of the sleeve 34 and of the corresponding internal threads of the jacking bush 36.

As can be seen in FIG. 2, O-ring seals are provided between the upper end flange 6 of the column tube 4 and the lower face of the end cap 8, and between the exterior of the piston rod 16 and the interior of the nut 38 past which it slides during adjustment. This is to contain any pressurising gas within the interior 40 of the chromatography column.

The interior of the clamp bush 24, i.e. the bore 30 and the annular space defined in the skirt 28, is filled with an incompressible fluid such as hydraulic oil. Thus, as the cap screw 32 is screwed home into the bore 30, the pressure in the hydraulic oil chamber within the clamp bush 24 increases and the thin walls of the skirt portion both radially inwardly of and radially outwardly of the annular oil space allows radial expansion of the skirt portion. Since the external surface of the skirt portion is constrained by the shrunk-on sleeve 34, this radial expansion results in radially inward displacement of the radially inwardly facing surface of the skirt portion 28, clamping against the plain exterior of the piston rod 16.

Conversely, withdrawing the cap screw 32 slightly allows release of the clamping action, to permit the piston rod 16 to be traversed rapidly axially along the column tube 4.

The operation of assembling the end cap 8 and the quick-release clamp 22 will be self-evident from the above description. However, the operation of a column with the end cap already assembled is as follows:

Initially the above-mentioned clamp which holds the end cap 8 on to the upper end flange 6 will have been released to allow unpacking of the chromatography column and the end cap 8 will have been removed along with the piston rod 16 and piston 14. The chromatography column can then be filled with an appropriate volume of appropriate separation media following which the piston 14 can then be introduced into the interior of the column tube (with the end cap 8 already placed on to the piston rod 16). Once the piston 14 has been introduced, the end cap 8 can be seated on the end flange 6 and clamped thereto by application of the clamp.

There are then various alternative ways of packing the bed:

(a) The piston rod can then be depressed to drive the piston 16 down the column tube 4 until the underside of the piston 11 abuts the upper surface of the bed of chromatography media in the column. Just prior to this point, or even after such contact has been attained, the cap screw 32 may be tightened home in order to clamp the piston rod within the skirt portion 28 of the clamp bush 24 and thereafter the vertical position of the piston 11 may be adjusted with high precision by rotating the piston rod 16 by use of the control wheel 18.

Thus the control wheel 18 can be used either simply to bring the piston, defining the upper end cell of the bed, into engagement with the bed, or to apply a preloading on the bed, or to adjust the loading in use of the bed.

(b) The end cap 8 also includes a pneumatic inlet 42 which can be used for pressurising gas to hold the piston down or to drive it further. When used in this pneumatic packing process; the end cap clamp assembly 22 will normally remain in the released configuration, allowing free sliding movement of the piston rod 16 through the clamp bush 24 under the influence of the pneumatic pressure applied through inlet 42. This will allow a fixed pressure, varying volume, bed mode to be adopted.

(c) Alternatively, pneumatic pressure can be applied through the inlet 42 in order to apply a pre-loading of the piston on the top of the bed of chromatography media, and then either the inlet 42 may be closed in order to hold a fixed position for the piston 14 or it may be left open and the liquid pressure applied thereto maintained constant so that any settling or expansion of the media in the bed during the chromatography process can be accommodated by vertical movement of the piston while maintaining the bed subject to a substantially constant head loading.

In use of the chromatography column, the liquid to be separated for analytical or production purposes is introduced through the piston rod 16 which is hollow. Preferably there is a hollow actuating shaft within the piston rod 16 (for the piston seal), as described in our simultaneous British Patent Application 9020450.4, through which passes a tube for the liquid to be separated whereby this liquid is fed to the piston 14 before passing through the screen carried by the piston.

Figure 3:
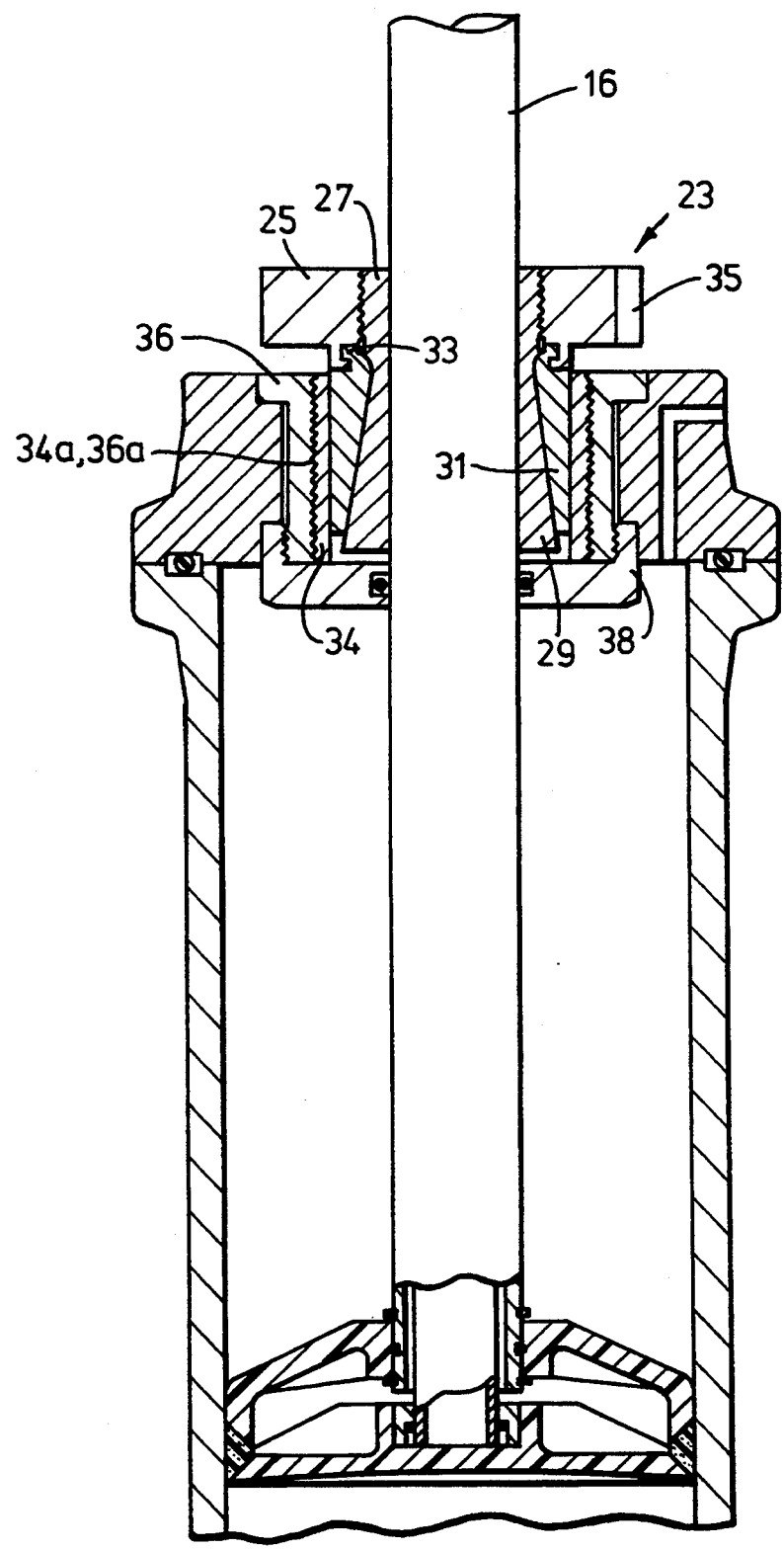
FIG. 3 is a view similar to FIG. 2 but showing an alternative embodiment of friction clamp.

FIG. 3 shows an alternative form of the clamping mechanism 23 comprising a lock ring 25 threaded on the upper end 27 of a collet structure 29 having an external conical surface at its lower portion for cooperating with an internal conical surface of a wedging portion 31 of the clamp rotatably connected to the lock ring 25 by means of an interdigitating ring and shoulder formation 33. The tapered portion 31 has the reinforcing ring 34 shrunk thereon, and this ring 34 is in turn threaded in the jacking bush 36 also shown in FIG. 2. Likewise, the lower end of the jacking bush 36 has the nut 38 threaded thereon.

When the friction clamp is to be engaged, the lock ring 25 is turned by means of a spanner engageable with flats (one of which is shown at 35 in FIG. 3) of the lock ring 25, and this causes the cooperating threads between the lock ring 25 and the upper end 27 of the collet structure 29 to drive the lock ring 25 downwardly, by virtue of a loose friction fit of the collet portion 29 on the piston rod 16 holding the collet structure 29 substantially stationary while the lock ring 25 rotates.

The downward thrust of the lock ring 25 drives the wedging portion 31 more firmly up the taper of the collet structure 29 to press the collet structure 29 firmly inwardly against the piston rod 16 to effect clamping.

To assist the efficiency of this clamping action, the collet structure 29 is preferably provided with several axial slits regularly spaced around its periphery, to render it more readily radially deformable.

When release of the clamp is required, the lock ring 25 is rotated in the reverse direction to back it upwardly relative to the collet structure 29, and the interdigitating ring structure 33 draws the wedging portion 31 upwardly to release the clamping action and hence to allow the collet sections of the collet structure 29 to relax their grip on the piston rod 16, thereby allowing release of the clamp.

As indicated at the outset, the ability to adjust the position of a chromatography column piston using a threaded piston rod is particularly advantageous but somewhat tedious in requiring a long time to traverse the piston during the packing and unpacking operations. Using the friction/screw clamp of the present invention allows the time taken for traversing to a position close to the desired final position of the piston during manual packing to be reduced considerably, while still allowing the screw-threaded final positioning due to cooperation of the threads of the sleeve 34 and the jacking bush 36 when the clamp bush 24 or collet structure 29 is clamped to the piston rod 16. Furthermore, as just indicated above, this possibility of a friction clamp system allows for manually operated and for automated pneumatic packing and unpacking, as desired.

We claim:

1. A chromatography column including: a column tube; a movable piston within the column tube; an axially slidable unthreaded piston rod carrying said piston; a releasable friction clamp for releasing said piston rod for rapid axial traversing of the piston and for clamping the piston rod at or near a desired final position; and means for fine adjustment of the position of the friction clamp axially relative to the column tube, for fine positioning of the piston relative to the column tube.

2. A chromatography column according to claim 1, wherein said means for fine adjustment of the height of said friction clamp relative to the column tube comprises a mechanical interconnection between the friction clamp and an associated end cap of the chromatography column.

3. A chromatography column according to claim 2, wherein said mechanical interconnection comprises screw threads on a first member secured to or forming part of said associated end cap and on a second member secured to or forming part of said friction clamp.

4. A chromatography column according to claim 3, wherein said friction clamp comprises a clamping collet structure able to fit loosely on said piston rod and a lock ring threadedly engageable with said collet structure and associated with a wedging portion of the clamp such that rotation of said lock ring relative to the collet structure in a first direction wedges the collets thereof radially inwardly to grip said piston rod whereas rotation in a second sense relative to said collet structure releases the collets to relax their grip on said piston rod.

5. A chromatography column according to claim 1, wherein said friction clamp comprises a hollow clamp bush having therewithin a hydraulic chamber communicating with a variable volume control chamber adjustable from outside the clamp bush to pressurize said hydraulic chamber of the clamp bush to expand a skirt portion of the bush for clamping against the piston rod.

6. A chromatography column according to claim 5, wherein said control chamber comprises a threaded bore and includes a cap screw the position of which can be adjusted to pressurize the hydraulic fluid within said bore.

7. A chromatography column according to claim 6, wherein said clamp bush is formed of stainless steel.

8. A chromatography column according to claim 5, wherein said clamp bush is formed of stainless steel.

9. A chromatography column according to claim 1, wherein said friction clamp comprises a clamping collet structure able to fit loosely on said piston rod and a lock ring threadedly engageable with said collet structure and associated with a wedging portion of the clamp such that rotation of said lock ring relative to the collet structure in a first direction wedges the collets thereof radially inwardly to grip said piston rod whereas rotation in a second sense relative to said collet structure releases the collets to relax their grip on said piston rod.

* * * * *